United States Patent
Del Rio et al.

(10) Patent No.: US 8,052,696 B2
(45) Date of Patent: Nov. 8, 2011

(54) SUTURE TENSIONING DEVICE

(75) Inventors: Eddy H. Del Rio, Royal Palm Beach, FL (US); William E. Anspach, III, Stuart, FL (US)

(73) Assignee: The Anspach Effort, Inc., Palm Beach Gardens, FL (US)

( * ) Notice: Subject to any disclaimer, the term of this patent is extended or adjusted under 35 U.S.C. 154(b) by 513 days.

(21) Appl. No.: 12/229,471

(22) Filed: Aug. 22, 2008

(65) Prior Publication Data

US 2010/0049248 A1    Feb. 25, 2010

(51) Int. Cl.
*A61B 17/04* (2006.01)

(52) U.S. Cl. ........ 606/144; 606/139; 606/103; 606/146; 606/148

(58) Field of Classification Search ............... 606/232, 606/148, 1, 103, 139, 144–146; 289/17; 242/338.4, 417.3, 419.7, 388, 388.1, 388.2, 242/388.3, 388.4, 388.6
See application file for complete search history.

(56) References Cited

U.S. PATENT DOCUMENTS

| | | | | |
|---|---|---|---|---|
| 4,004,485 A | * | 1/1977 | Hiscott | 84/207 |
| 4,832,666 A | * | 5/1989 | Henderson | 474/135 |
| 4,935,027 A | * | 6/1990 | Yoon | 606/146 |
| 5,693,059 A | * | 12/1997 | Yoon | 606/139 |
| 7,963,972 B2 | * | 6/2011 | Foerster et al. | 606/139 |
| 2003/0208210 A1 | * | 11/2003 | Dreyfuss et al. | 606/144 |
| 2005/0049598 A1 | * | 3/2005 | West et al. | 606/72 |
| 2007/0225736 A1 | * | 9/2007 | Zeiner et al. | 606/148 |
| 2008/0275477 A1 | * | 11/2008 | Sterrett et al. | 606/148 |
| 2009/0146357 A1 | * | 6/2009 | Pietrantoni et al. | 269/254 CS |
| 2009/0326562 A1 | * | 12/2009 | White et al. | 606/148 |
| 2009/0326563 A1 | * | 12/2009 | White et al. | 606/148 |

* cited by examiner

*Primary Examiner* — Darwin Erezo
*Assistant Examiner* — Todd J Scherbel
(74) *Attorney, Agent, or Firm* — Norman Friedland

(57) ABSTRACT

A suture tensioning apparatus for tightening the suture used to tie a tissue of a patient to the bone of the patient so that the tissue will cinch to the bone. A lever is mounted on a stub shaft that is supported to a base member and is movable in a lateral position. A pair of spaced spools are mounted on the lever and the reach of the suture is wrapped around each of the spools. Means, including a coil spring wrapped around the stub shaft is connected to the lever and a rotatable dome. The movement of the lever causes the lower portion of the coils to unwrap around the stub shaft, and rotation of the dome causes the upper portion of the coils to unwrap whereby the movement of the coil spring forces the lever to return to its original position. The tensioning apparatus can be incorporated into an existing suture gun or can be made integral therewith.

8 Claims, 2 Drawing Sheets

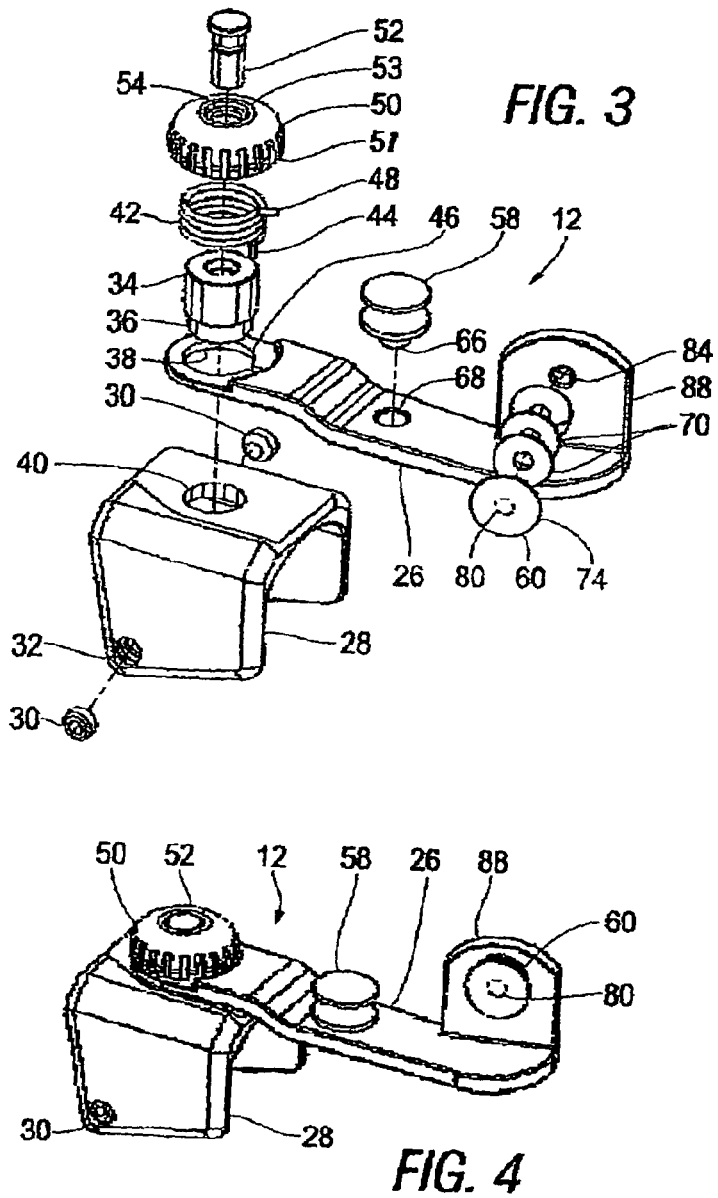
FIG. 3
FIG. 4
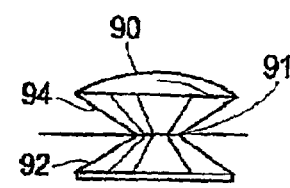
FIG. 5
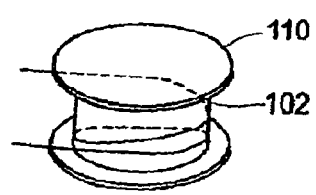
FIG. 6

SUTURE TENSIONING DEVICE

RELATED APPLICATIONS

Not applicable

FEDERALLY SPONSORED RESEARCH OR DEVELOPMENT

Not applicable

TECHNICAL FIELD

This invention relates to medical apparatus and to a surgical procedure in which a medical tool is used for insertion of an anchor into the bone of a patient and suture is connected to the tissue and the anchor for tying the soft tissue to the bone and particularly to mechanism carried on the medical tool (suture gun) that attaches to the suture so as to assist the surgeon to apply tension to the suture. The suture serves to tie the soft tissue to the bone and the tensioning of the suture serves to cinch the soft tissue to the bone during a surgical procedure. The medical apparatus can be in the form of an add-on to existing suture guns or it can be made integral with the suture gun.

BACKGROUND OF THE INVENTION

As is well known in the medical field, there is an increasingly occurring problem where connective tissue, such as tendons and ligaments, tear or detach from the associated bone. While this invention is not limited to the method of incisions used in this type of operation, there is a trend in this type of operation to use arthroscopic surgical techniques rather than cutting large incisions in the tissue of the patient for performing the reattachment operation in this medical procedure. A typical problem that is the concern of this invention, although not the only one, is the tear or detachment of the soft tissue in the rotator cuff as to where the supraspinatus tendon separates from the humerus. In this type of medical procedure the advent of the knotless suture has played an important roll in allowing the surgeon to perform this type of operation using arthroscopic techniques. In this type of operation, typically, an anchor is inserted into the bone and suture is wrapped around the tendon and connected to the anchor. Obviously, the suture requires a given amount of tension so as to cinch the tendon to the bone while not adversely affecting the intergrity of the suture. A good example of a suture applied in this manner is described in U.S. Pat. No. 7,144,415 granted to Eddy H. Del Rio and William E. Anspach, III, the joint inventors of the present invention, which is incorporated in its entirety herein. As described in this patent, the surgeon before clamping the suture pulls on the reaches of the suture so as to apply the proper amount of tension in order to cinch the tendon to the bone. A problem associated with this procedure is that the amount of force that the surgeon requires to pull the suture to the desired position is either difficult because of the necessary force required or that the surgeon has other things going on while he is pulling on the suture and it may be cumbersome to make that pull. Accordingly, this invention is intended to solve this problem by providing mechanism that applies the tension necessary to cinch the tendon to the bone and facilitate this action so that the task of cinching the tendon to the bone is less cumbersome.

SUMMARY OF THE INVENTION

An object of this invention is to provide improved means for applying tension to a suture used for connecting soft tissue to bone.

A feature of this invention is to provide an add-on to a suture gun that includes a rotatable lever adapted to be handled by the surgeon that attaches the suture ends thereto and allows the surgeon to rotate the lever to apply tension to the suture. The tensioning mechanism can be made integral with the suture gun.

The foregoing and other features of the present invention will become more apparent from the following description and accompanying drawings

BRIEF DESCRIPTION OF THE DRAWINGS

FIG. 3 is an exploded view of the tensioning device of this invention;

FIG. 4 is the tensioning device of FIG. 3 shown in the assembled condition;

FIG. 5 is an enlarged view in schematic of the spool depicted in FIG. 1 and illustrating the spool used in connection with the tensioning device of this invention; and FIG. 6 is an enlarged view in schematic of the other spool depicted in FIG. 1 and illustrating the suture wrapped around to hold the suture in place.

DETAILED DESCRIPTION OF THE INVENTION

Figure 1:
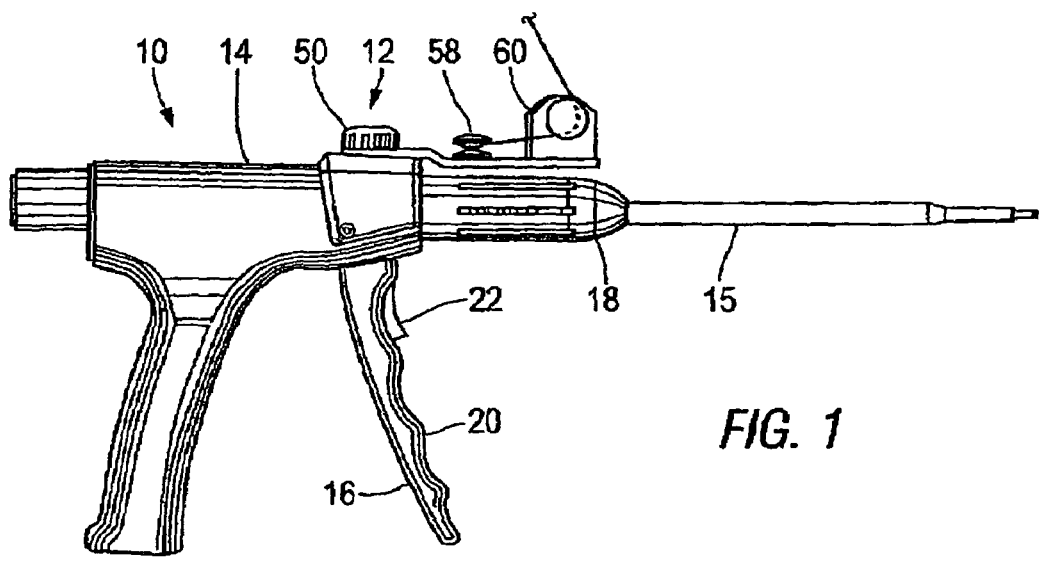
FIG. 1 is a view in elevation illustrating this invention when added to a commercially available suture gun.

While this invention is being described in its preferred embodiment as being attached to a commercially available suture gun, it should be understood by one skilled in this art, that the suture tensioning device of this invention can be incorporated into the original design of the suture gun. Hence, this invention is capable of modifying existing suture guns or being part of the original manufactured suture gun.

The invention is best understood by referring to all of the Figures, where the suture gun is generally illustrated by reference numeral 10 and the tensioning apparatus is generally illustrated by reference numeral 12. As mentioned earlier the suture gun 10 is commercially available as for example from the assignee, The Anspach Effort, Inc. of Palm Beach Gardens, Fla., and comprises a main housing 14 shaped in the form of a pistol with a handle 16. Chuck 18 on the distal end of the main housing 14 serves to hold the end of the rivet shaft 15 that carries the rivet (not shown). The gun includes a trigger 20 that serves to draw the rivet shaft 15 toward the handle 16 for releasing the rivet shaft from the rivet. A mini-trigger 22 is for the purpose of locking the rivet shaft in a rigid position so that the surgeon can force or guide the rivet into the opening formed in the bone of the patient. If necessary, the proximate end of the suture gun 10 is formed in a quasi mallet base so that the surgeon can, with the use of a mallet or hammer, knock the rivet into place. Depressing the trigger 22 frees the rivet shaft and allows the main trigger 20 to be depressed in order to translate the rivet shaft 15 As this is a well known device, for the sake of convenience and simplicity, one should refer to the commercially available suture gun or literature relating thereto in order to obtain its details.

The purpose of this invention is to allow the surgeon in a simple and uncomplicated manner to assure that the suture that is attached to the tendon and ultimately locked by the knotless suture lock mechanism to the anchor of the type, for example, that is described in U.S. Pat. No. 7,144,415 granted to the joint inventors of this patent application on Dec. 5, 2006 entitled ANCHOR/SUTURE USED FOR MEDICAL PROCEDURES Suffice it to say, before the suture is locked in place, the surgeon would want the suture to be sufficiently tight so that the suture causes the tendon to cinch to the bone. Heretofore, the surgeon would merely pull on the reaches of the suture and pull until the surgeon was under the impression that there was sufficient tension on the suture to assure the cinching.

According to the present invention and as best seen in FIGS. 3 and 4, the tensioning apparatus 12 comprises a main lever 26 and a U-shaped adapter member 28 that fits over the top of the suture gun 10. The U-shaped adapter member 28 is mounted to the gun and held into place by the locking nuts 30 that fit through threaded apertures 32 formed on the side wall of the main housing 14. A main rigid post or stub shaft 34 includes a smaller diameter portion 36 that fits into aperture 38 and is dimensioned to snuggly fit into the aperture 40 formed in the U-shaped adapter member or base member 28. Coil spring 42, that will be described in detail herein below, includes a depending end 44 that fits into slot 46 formed on lever 26 adjacent to the aperture 38. Another depending end 48 formed on the top end of the coil spring 42 that extends radially outward fits into slot 51 formed in the top of rotatable dome shaped member 50. This sub-assembly is locked into place by the pin 52 that fits into the central recess 54 formed on the top end of post 34 and through the aperture 53 centrally extending through the dome 50. Lever 26 that is mounted on the smaller diameter portion 36 of rigid post 34 is rotatable around the rigid post 34 and may be stepped to conform to the shape of the top of the suture gun. The lever 26 carries a pair of spools 58 and 60 that serve to hold the reaches of the suture as will be described herein below. Spool 58 is rigidly secured to lever 26 by the circular projected portion 66 formed on the bottom of the spool 58 which snugly fits into the aperture 68 formed in the lever 26. Spool 60 is comprised of a pair of inverted Bellville washers 70 that are secured by the end plate 74 by virtue of stub shaft 80 that fits through the central apertures of the Bellville washers 70 and is snuggly fitted into aperture 84 that is formed in the vertical projection portion 88 of lever 26. The assembled unit is shown in FIG. 4.

In operation the reach(s) of the suture is pulled taut by the surgeon and then wrapped around the spool 58 and the further end of the reach is then wrapped around the spool 60 where it slides between bevel washers 70 to be firmly held into place. Preferably the reach is double wound around spool 58 to avoid slippage. The lever 26 is then pulled laterally by the surgeon in the position illustrated by the arrow A and when the suture is at is maximum tension, i.e. when the lever stops its rotation, the suture is then sufficiently tight to force the tendon to cinch to the bone.

The initial lateral movement of lever 26 causes the lower end of coil spring 42 to unwind to cause a portion thereof to move away from post 34 and unlocks the coil spring 42 and allows the lever 26 and a portion of coil spring 42 to rotate or slightly unwind about the post 34. The lever 26 is ultimately automatically returned to its original position by virtue of coil spring 42. This is accomplished by rotating dome 50 which, in turn, causes the upper end of coil spring 42 via the projection 48 to move away or unwind from the post 34 and hence, causing the spring to relieve force on the stub shaft 34 which allows the coil spring 42 to drive the lever 26 back to the original position. It is apparent from this description that the spring normally locks the lever 26 in place and when the lever 26 is initially rotated the lower end of coil spring 42 via the depending end 44 unwinds the lower end of the coil spring away from the post 34 and allows the lever 26 to rotate. After lever 26 reaches its destination, i.e. when the suture is fully tensioned, the initial rotation of the dome 50 by the user causes the upper end of coil spring 42 via the depending end 48 to unwind. This serves to unlock the upper portion of coil spring from the post 34 wherein the lever 26 by virtue of the load on the spring by the previous movement of lever 26 rotates lever 26 back to its original position.

Figure 2:
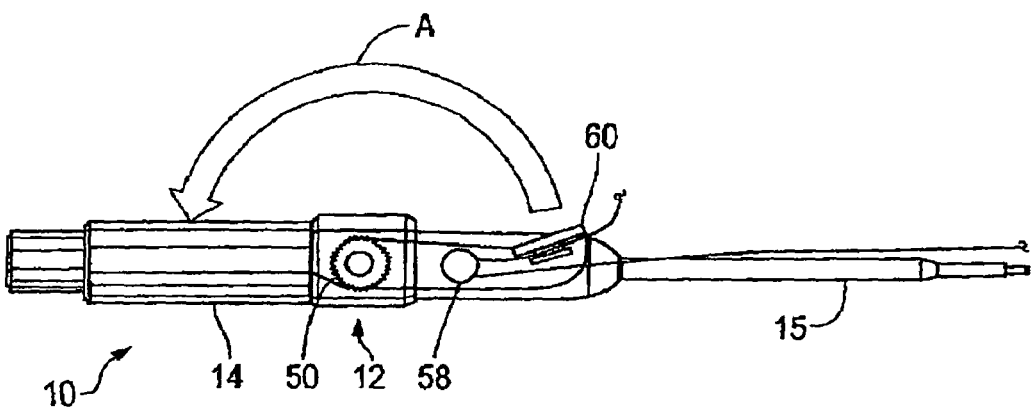
FIG. 2 is a top plan view of the suture tensioning device of this invention and the operation thereof.

The spools depicted in FIGS. 5 and 6 schematically illustrates examples of spools that can be utilized with the present invention. It will be noted that spool 90, as best seen in FIG. 5, corresponding to the spool 60 of FIGS. 1-4, includes opposing tapered portions defined by the bevel washers 92 and 94 forming a small diameter annulus 91. This design allows the suture to force the bevel washers slightly away from each other and fits where the suture can then fit between the two washers providing an adequate locking feature of the suture in the spool. Spool 100, corresponding to spool 58 depicted in FIGS. 1-4, illustrates a cylindrical inner portion 102 with the suture double wrapped there-around. Obviously, the shape of the spool can take many forms so long as when the suture is wound thereon, it will not slip when the lever 26 actuated.

What has been shown by this invention is a tensioning device that can be utilized with a commercially available suture gun that allows the surgeon with the use of one hand to apply tension to a suture with relative ease. Obviously, the original manufacture of the suture gun can be made to include the tensioning device of this invention.

Although this invention has been shown and described with respect to detailed embodiments thereof, it will be appreciated and understood by those skilled in the art that various changes in form and detail thereof may be made without departing from the spirit and scope of the disclosed invention.

We claim:

1. A suture tensioning apparatus operable by a user for adding tension to a suture used in surgery and said suture tensioning device including a base member,
    a lever pivotally connected to said base member and locked into position whenever said lever is in a non-rotating condition,
    an engagable member on said lever adapted to be engaged by the user,
    a first spool mounted on said lever and a second spool mounted on said engagable member,
    said first spool adapted to have a portion of said suture wrapped there-around and said second spool adapted to have an additional portion of said suture wrapped there-around,
    said lever when rotated by the user is movable in an operating position wherein said rotation of said lever unlocks said lever and allows said lever to rotate,
    whereby, the rotation of said lever repositions said first spool, said second spool and said suture so as to pull said suture and thereby increasing the tension thereof,
    a fixed vertical shaft mounted on said base member and rotatably supporting said lever on one end,
    said first spool mounted on said lever intermediate the ends thereof and extending in a vertical direction,
    said engagable member mounted on the end of said lever remote from said fixed vertical shaft,
    said second spool mounted on said engagable member and extending horizontally,
    whereby the suture portion is first wrapped around said first spool and said additional portion of said suture is secondly wrapped around said second spool,
    wherein said fixed vertical shaft includes a central recess, a dome, a pin mounted through a central aperture in said dome and into said central recess for rotation thereof, the dome member is mounted at the top of said fixed vertical shaft and rotatably mounted on the top end of thereon, a coil spring surrounding said fixed vertical shaft and bearing there against to prevent rotation thereof, said coil spring having an upper projection and a lower projection, wherein the upper projection fits into a slot formed in said dome and said lower projection fits into a slot formed on said lever, wherein rotation of said lever allows the lower end of said coil spring to unwind and rotation of said dome allows the upper end of said coil spring to unwind wherein after said lever reaches its full extension, said coil spring causes said lever to return to the original position.

2. A suture tensioning apparatus as claimed in claim 1 wherein said base member is U-shaped defining a pair of downwardly projecting arms, said arms adapted to straddle the a suture gun and means for mounting said suture tensioning apparatus to the suture gun.

3. A tensioning apparatus for causing suture tying tissue to a bone of a patient to be drawn to a taut condition comprising a main body, a fixed stub shaft supported to said main body and extending in an upright position, a lever pivotally connected to one end of said fixed stub shaft and rotatably mounted thereon, a dome pivotally mounted to said fixed stub shaft at the end remote from said lever, a coil spring surrounding said fixed stub shaft and bearing there-against to prevent rotary motion of said lever, a pair of spaced spools mounted on said lever and adapted to have a reach of the suture to be wrapped around each of said pair of spaced spools, wherein the pivoting of said lever by the user thereof causes the suture to become taut.

4. A tensioning apparatus for causing suture tying tissue to a bone of a patient to be drawn to a taut condition as claimed in claim 3 including means for returning said lever to its original position, said means including the coil spring wrapped surrounding said stud shaft and having a lower extension portion and a upper extension portion, said lower extension portions fitting into a slot formed on said lever and said upper extension portion fitting into a slot formed on said dome, whereby said rotation of said lever causes the lower portion of said coil spring to unwrap from said stud shaft and rotation of said dome causes the upper portion of said coil spring to unwrap from said stud shaft allowing the force of said coil spring to return said lever to its original position.

5. A tensioning apparatus for causing suture tying tissue to a bone of a patient to be drawn to a taut condition as claimed in claim 4 wherein one of said spools comprises a first Bellville washer and a second Bellville washer inverted relative to said first Bellville washer whereby the suture fits between said first Bellville washer and said second Bellville washer and held there-between by the forces exerted thereby.

6. A tensioning apparatus for causing suture tying tissue to a bone of a patient to be drawn to a taut condition as claimed in claim 5 including an upstanding member carried by said lever and wherein one of said spools is mounted on said upstanding member.

7. A tensioning apparatus for causing suture tying tissue to a bone of a patient to be drawn to a taut condition as claimed in claim 6 wherein said other spool is axially and radially spaced from said one of said spools.

8. A tensioning apparatus for causing suture tying tissue to a bone of a patient to be drawn to a taut condition wherein said main body as claimed in claim 7 includes depending arms adapted to be supported to a suture gun wherein said tensioning apparatus is supported thereby to the suture gun.

* * * * *